United States Patent
Grass et al.

(10) Patent No.: US 11,253,217 B2
(45) Date of Patent: Feb. 22, 2022

(54) APPARATUS FOR VESSEL CHARACTERIZATION

(71) Applicant: KONINKLIJKE PHILIPS N.V., Eindhoven (NL)

(72) Inventors: Michael Grass, Hamburg (DE); Dirk Schaefer, Hamburg (DE); Arjen Van Der Horst, Tilburg (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 273 days.

(21) Appl. No.: 15/761,056

(22) PCT Filed: Sep. 15, 2016

(86) PCT No.: PCT/EP2016/071908
§ 371 (c)(1),
(2) Date: Mar. 16, 2018

(87) PCT Pub. No.: WO2017/046288
PCT Pub. Date: Mar. 23, 2017

(65) Prior Publication Data
US 2018/0242941 A1      Aug. 30, 2018

(30) Foreign Application Priority Data

Sep. 16, 2015   (EP) .................................... 15185452

(51) Int. Cl.
*G06T 7/60*        (2017.01)
*A61B 5/107*      (2006.01)
(Continued)

(52) U.S. Cl.
CPC ............ *A61B 6/504* (2013.01); *A61B 5/1076* (2013.01); *A61B 6/12* (2013.01); *A61B 6/466* (2013.01);
(Continued)

(58) Field of Classification Search
CPC .... G16H 50/50; G16H 30/40; A61B 5/02007; A61B 34/10; A61B 6/504; A61B 5/026;
(Continued)

(56) References Cited

U.S. PATENT DOCUMENTS

| | | | |
|---|---|---|---|
| 4,875,165 A | 10/1989 | Fencil et al. | |
| 7,731,500 B2 * | 6/2010 | Feygin | G09B 23/285 434/272 |

(Continued)

FOREIGN PATENT DOCUMENTS

| | | |
|---|---|---|
| WO | 2013001388 A1 | 1/2013 |
| WO | 2013024418 A1 | 2/2013 |

OTHER PUBLICATIONS

Koning et al., Advanced contour detection for three-dimensional intracoronary ultrasound: a validation—in vitro and in vivo, Aug. 2002 [retrieved Sep. 29, 2021], The Inter Jour of Cardiovascular Imaging, vol. 18, pp. 235-248. Retrieved: https://link.springer.com/article/10.1023/A:1015551920382 (Year: 2002).*

(Continued)

*Primary Examiner* — Matthew C Bella
*Assistant Examiner* — Dennis Rosario (57) ABSTRACT

A three-dimensional morphological vessel model (20) can be obtained by assigning diameters (14,15) along the vessel derived from a two-dimensional morphological projection (10) at locations in the three-dimensional model defined by the temporal locations (21,22) of a trackable instrument (5). An apparatus (7), a system (1) and a method (100) for use of the system (1) in characterizing the vessel of a living being (2) by rendering a three-5 dimensional morphological vessel model (20) are presented.

11 Claims, 6 Drawing Sheets

(51) Int. Cl.
  *A61B 6/00* (2006.01)
  *A61B 6/12* (2006.01)
  *G06T 7/246* (2017.01)
  *A61B 5/0265* (2006.01)

(52) U.S. Cl.
  CPC .............. *A61B 6/481* (2013.01); *A61B 6/507* (2013.01); *A61B 6/5217* (2013.01); *G06T 7/251* (2017.01); *G06T 7/60* (2013.01); *A61B 5/0265* (2013.01)

(58) Field of Classification Search
  CPC ......... A61B 6/5217; A61B 8/06; A61B 5/021; A61B 2034/107; A61B 34/25; A61B 8/5223; A61B 5/6852; A61B 8/0891; G06T 7/0012; G06T 2210/41; G06T 17/00; G06T 2200/04; G06T 2207/30104; G06T 7/62; G06T 2207/30101; G06T 2207/30172; G06T 2207/10116; G06T 2207/10072; G06T 2207/10081; G06T 2207/20044; G06T 2207/10132; G06T 7/11; G06T 2207/30048; G06T 2211/404; G06T 7/149; G06T 11/008; G06T 2207/10088; G06T 17/20; G06T 2207/10101; G06F 30/23
  See application file for complete search history.

(56) References Cited

U.S. PATENT DOCUMENTS

| | | | | |
|---|---|---|---|---|
| 7,738,626 | B2* | 6/2010 | Weese | A61B 6/481 |
| | | | | 378/41 |
| 7,901,348 | B2* | 3/2011 | Soper | A61B 1/00009 |
| | | | | 600/117 |
| 9,351,698 | B2* | 5/2016 | Dascal | G06T 7/11 |
| 2004/0116813 | A1* | 6/2004 | Selzer | A61B 5/02007 |
| | | | | 600/467 |
| 2005/0033114 | A1* | 2/2005 | Geiger | G06T 7/12 |
| | | | | 600/101 |
| 2005/0182295 | A1* | 8/2005 | Soper | A61B 1/00172 |
| | | | | 600/117 |
| 2006/0064006 | A1 | 3/2006 | Strommer | |
| 2007/0223794 | A1 | 9/2007 | Preiss | |
| 2009/0182224 | A1 | 7/2009 | Shmarak | |
| 2010/0130878 | A1* | 5/2010 | Lasso | G06F 19/00 |
| | | | | 600/500 |
| 2011/0019892 | A1* | 1/2011 | Rahn | A61B 6/466 |
| | | | | 382/131 |
| 2011/0206248 | A1* | 8/2011 | Ruijters | G06T 7/66 |
| | | | | 382/128 |
| 2014/0142398 | A1* | 5/2014 | Patil | A61B 6/463 |
| | | | | 600/301 |
| 2015/0161790 | A1 | 6/2015 | Akihito | |
| 2015/0262388 | A1* | 9/2015 | Ishii | G06T 7/30 |
| | | | | 382/131 |
| 2016/0113699 | A1* | 4/2016 | Sverdlik | A61N 7/00 |
| | | | | 606/27 |
| 2019/0110839 | A1* | 4/2019 | Rafii-Tari | A61B 34/10 |

OTHER PUBLICATIONS

Reiber et al., State of the Art in Quantitative Coronary Arteriography as of 1996, 1996 [retrieved Sep. 29, 2021], Cardiovascular Imaging. Developments in Cardiovascular Medicine, vol. 186, pp. 39-56. Retrieved: https://link.springer.com/chapter/10.1007/978-94-009-0291-6_4#citeas (Year: 1996).*

Von Birgelen et al., Morphometric analysis in three-dimensional intracoronary ultrasound: An in vitro and in vivo study performed with a novel system for the contour detection of lumen and plaque, Sep. 1996 [retrieved Sep. 29, 2021], American Heart Journal, vol. 132, Issue 3, pp. 516-527. Retrieved: (Year: 1996) https://www.sciencedirect.com/science/article/pii/S0002870396902331 (Year: 1996).*

* cited by examiner

APPARATUS FOR VESSEL CHARACTERIZATION

CROSS-REFERENCE TO PRIOR APPLICATIONS

This application is the U.S. National Phase application under 35 U.S.C. § 371 of International Application No. PCT/EP2016/071908, filed on Sep. 15, 2016, which claims the benefit of International European Application No. EP15185452.8, filed on Sep. 16, 2015. These applications are hereby incorporated by reference herein.

FIELD OF THE INVENTION

The present invention relates to an apparatus, a system and method for characterization of vessels and for vessel modeling.

BACKGROUND OF THE INVENTION

A typical technique for identifying stenotic regions in a blood vessel is using angiography, whereas the functional impact of the stenosis is quantified with the fractional flow reserve (FFR) method. FFR is calculated from the ratio of pressures at the distal and proximal ends of the stenosis, measured with a sensor positioned at the tip of a wire. According to the FFR value the severity of the stenosis is established, specifically whether the stenosis limits blood flow within the vessel to an extent that treatment is required. Common treatment options include angioplasty, stenting or bypass.

Angiography, a fluoroscopy imaging technique in conjunction with radio-opaque contrast agents, can be used to visualize the vasculature of a patient.

U.S. Pat. No. 4,875,165 A describes a method for determination of three-dimensional structure in biplane angiography, including determining the distances of perpendicular lines from the focal spots of respective x-ray sources to respective image planes and defining the origin of each biplane image as the point of intersection with the perpendicular line thereto, obtaining two biplane digital images at arbitrary orientations with respect to an object, identifying at least eight points in both images which correspond to respective points in the object, determining the image coordinates of the eight identified object points in the respective biplane unknowns based on the image coordinates of the object points and based on the known focal spot to image plane distances for the two biplane images; solving the linear equations to yield the eight unknowns, which represent the fundamental geometric parameters of the biplane imaging system; using the fundamental parameters to calculate the three-dimensional positions of the object points identified in the biplane images; and determination of the three-dimensional positions of the vessel segments between the object points.

WO 2013001388 A1 discloses a method, and system for providing a live 3D image of a body lumen. The 3D shape of a flexible surgical tool in the body lumen is determined using optical shape sensing. An x-ray image is taken of the body lumen, with at least one of the body lumen and the surgical tool being radiopaque. The determined 3D surgical tool shape is registered to the x-ray image.

SUMMARY OF THE INVENTION

It is an object of the invention to provide an apparatus for a simpler and more intuitive characterization of vessels of living beings.

According to a first aspect of the invention, this object is realized by an apparatus for characterizing a vessel of a living being, the apparatus comprising:
a processor for processing measurement information, wherein the apparatus is configured to be coupled to:
a tracking unit for measuring temporal location information of a trackable instrument in a vessel,
an imaging unit for generating morphological projection information of the vessel;
the processor is configured to:
derive a first diameter of the vessel from the morphological projection information corresponding to a first temporal location of a distal portion of the instrument,
derive a second diameter of the vessel from the morphological projection information corresponding to a second temporal location of the distal portion of the instrument, and
assign the first and second diameters of the vessel in a three-dimensional morphological model of the vessel at two locations defined by a relative position between the first and second temporal locations of the distal portion of the instrument.

Characterization of vessels is improved in that the diameter of the vessel is provided in a three-dimensional model of the vessel morphology, based on computation of the diameter from morphological projection information combined with the temporal location information of the tracked device. A major benefit is that a single angiographic projection is sufficient for construction of the three-dimensional morphological vessel model, and that the three-dimensional model is generated as the distal portion (e.g. tip or a radiopaque marker) of the instrument moves within the vessel lumen. The three-dimensional model is augmented with the withdrawal of the instrument, therefore a three-dimensional model is presented to the user only for the relevant segment of the vessel through which the distal portion of the instrument has been maneuvered, making the information presented to the user simpler and the interpretation of the information more intuitive. In an embodiment of the apparatus, the temporal location information of the instrument processed by the processor is derived from electromagnetic signals. Electromagnetic tracking of instruments is one of the typical localization techniques, whereby an electromagnetic field is detected by an electromagnetic sensor integrated into the instrument, and the temporal location of the senor in the electromagnetic field is derived from the strength of the signal.

In an embodiment of the apparatus, the temporal location information of the instrument processed by the processor is derived from laser radiation. Optical shape sensing is a technology that uses reflections of laser radiation from multiple optical fibers or from a multi-core optical fiber integrated into an instrument to measure local strains to which the instrument is exposed. The shape of the optical fibers, hence that of the instrument, is derived by processing optical reflection signals from within the optical fibers, received by a detector. The advantage of optical shape sensing over electromagnetic tracking is that the full three-dimensional shape of the instrument is known at all instances, whereas with electromagnetic tracking only the discrete positions of the electromagnetic sensors integrated into the instrument can be derived.

In an embodiment of the apparatus, the first and second temporal location information indicative for the location of the instrument in the vessel originate at same phase of a cyclical cardiac motion. Assigning the first and second diameters of the vessel in a three-dimensional morphological model based on gating to the phase of the cyclical cardiac and/or respiratory motion is critical in instances where real-time assessment is carried out on the condition of coronary arteries, with significant motion due to heart beat and respiration.

In an embodiment the apparatus further comprises a display, and the processor is configured to render a graphical representation of the three-dimensional morphological model with the assigned first and second diameters on the display. Visual aspect of the three-dimensional vessel model supports assessment of the condition of the vasculature, since stenotic regions are represented by a significant narrowing of the vessel, whereas aneurysms have a bulging aspect.

According to a second aspect of the invention a system comprises:
- the apparatus for characterizing a vessel of a living being,
- the trackable instrument for introduction into the vessel of the living being,
- the tracking unit for measuring temporal location information of the instrument in the vessel,
- the imaging unit for generating morphological projection information of the vessel. The trackable instrument comprises at least an electromagnetic sensor for sensing an electromagnetic field generated by the tracking unit, or at least an optical fiber for sensing strain to which the instrument is exposed when the tracking unit transmits and receives laser radiation from within the at least an optical fiber. A radiological imaging unit such as a fluoroscopy system or a system used for x-ray computed tomography, capable of providing radiographic projection, can be used for acquiring the morphological information of vessels by angiography. Other imaging techniques suitable for acquiring morphological information of vessels may however be used, such as ultrasound imaging, or magnetic resonance imaging. The tracking unit may be integrated into the imaging unit. The trackable instrument may comprise markers traceable with the imaging unit used for acquiring morphological information of the vessels. The markers on the instrument are recognizable with the respective imaging modalities, for instance ultrasound reflecting or absorbing markers in ultrasound imaging.

In an embodiment of the system, the trackable instrument comprises a sensor for measuring physiological information, and the processor is configured to assign at least a first physiological information to the three-dimensional morphological model of the vessel at the location defined by the first temporal location of the instrument. In an alternative embodiment, the processor is further configured to assign at least a second physiological information to the three-dimensional morphological model of the vessel at the location defined by the second temporal location of the instrument. Assigning physiological information to the three-dimensional model supports the physician in assessment of vessel condition, for instance change in visual aspect of the model due to narrowing or broadening vessel branch, by confirmation of a variation of pressure, FFR, blood flow velocity or blood flow resistance values.

According to further aspect of the invention a method for characterizing a vessel of a living being comprises:
- introducing a trackable instrument into the vessel,
- measuring temporal location information of the instrument in the vessel,
- generating morphological projection information of the vessel,
- deriving a first diameter of the vessel from the morphological projection information corresponding to a first temporal location of a distal portion of the instrument,
- deriving a second diameter of the vessel from the morphological projection information corresponding to a second temporal location of the distal portion of the instrument, and
- assigning the first and second diameters of the vessel in a three-dimensional morphological model of the vessel at two locations defined by a relative position between the first and second temporal locations of the distal portion of the instrument.

In an embodiment of the method
- deriving the first and second diameters and measuring the first and second temporal locations of the instrument are performed for consecutive phases of a cyclical motion, and
- assigning the first and second diameters of the vessel in the three-dimensional morphological model of the vessel at two locations defined by the relative position between the first and second temporal locations of the distal portion of the instrument is performed for respective consecutive phases of the cyclical motion.

In an embodiment, the method further comprises the step of rendering a graphical representation of the three-dimensional morphological model on a display. The visual representation of the three-dimensional morphological model enables rapid assessment of various structural and functional nonconformities, such as vessel stenosis and/or presence of aneurysms.

Additional aspects and advantages of the invention will become more apparent from the following detailed description, which may be best understood with reference to and in conjunction with the accompanying drawings.

DETAILED DESCRIPTION OF EMBODIMENTS

Figure 1:
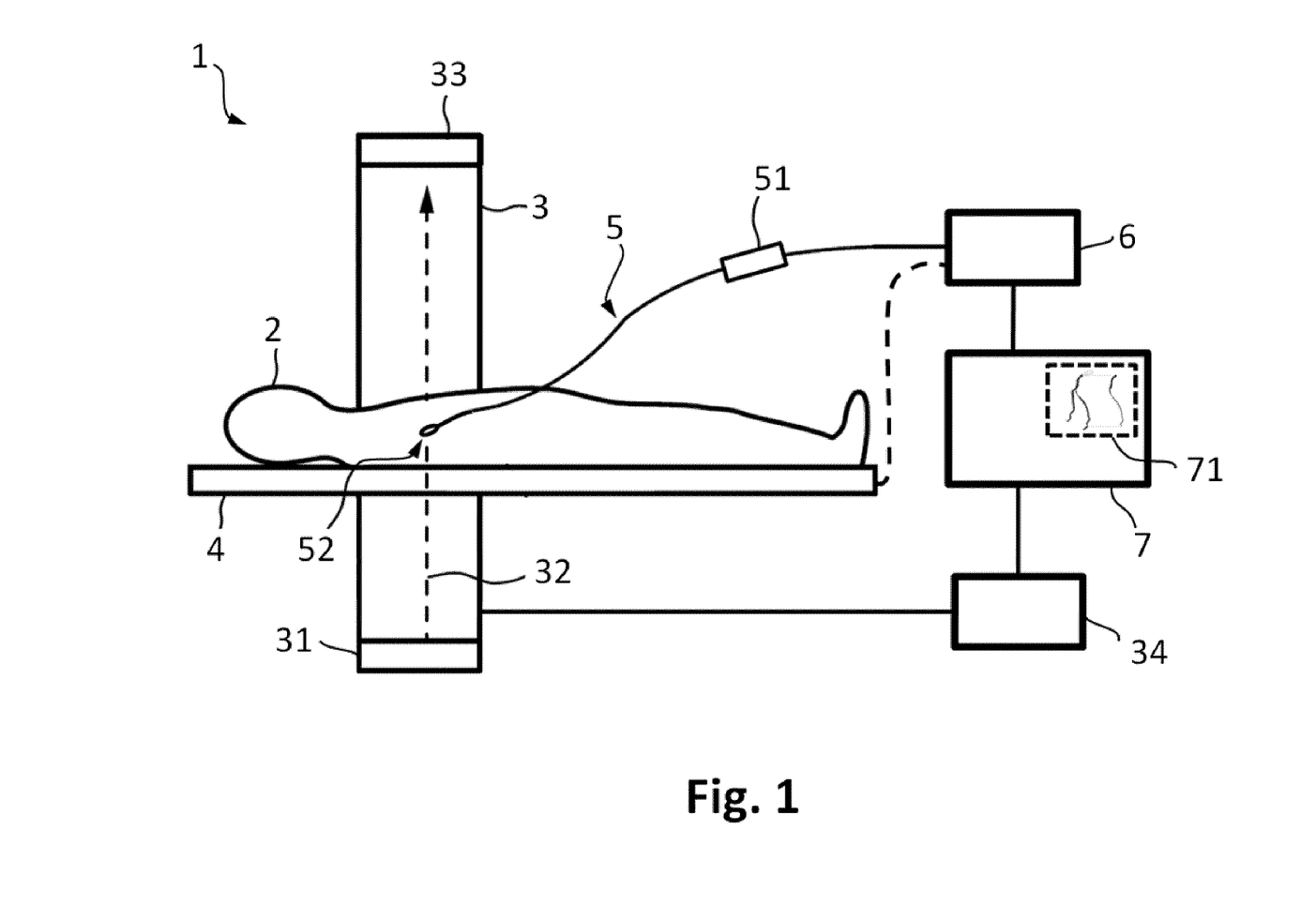
FIG. 1 shows schematically and exemplarily an embodiment of a system for characterizing a vessel of a living being, according to the invention.

FIG. 1 shows schematically and exemplarily an embodiment of a system 1 according to the invention for characterizing a vessel of a living being 2 such as a person or an animal. In this embodiment, the system comprises a radiological imaging unit 3 for acquiring angiographic projection of the vessel structure of interest upon injection of a contrast agent bolus in the targeted vasculature. The radiological imaging unit 3 comprises an x-ray source 31 for emitting x-rays 32 traversing the person 2 lying on the support means 4. The radiological imaging unit 3 further comprises an x-ray detector 33 for detecting the x-rays 32 after having traversed the person 2. The x-ray detector 33 is adapted to generate detection signals being indicative of the detected x-rays 32. The detection signals are transmitted to a fluoroscopy control unit 34, which is adapted to control the x-ray source 31, the x-ray detector 32 and to generate two-dimensional morphological projection information depending on the received detection signals. The injection of the radiological contrast agent bolus in the targeted vasculature is performed with an instrument 5, which may be an interventional catheter. The instrument 5 comprises a lumen extending from the handgrip 51 to the distal tip 52 positioned at the target site for contrast agent bolus injection. Alternatively, the instrument may comprise an opening of the lumen on the sidewall of the elongated body, so that a contrast agent bolus can be injected at a different site in the vessel than where the distal tip 52 is located.

The system further comprises a tracking unit 6 for measuring temporal location information indicative for the location of the instrument in the vasculature of the person 2. Tracking of the temporal location of the instrument may be based on one of an electromagnetic, an optical or an ultrasound principle. Electromagnetic tracking of instruments is based on detection of an electromagnetic field by an electromagnetic sensor. The electromagnetic sensor is typically integrated into the distal tip 52 of the instrument 5, whereas the electromagnetic field generator is placed in the vicinity of the targeted vasculature. The field generator may be movably attached to either the support means 4 of the person 2 or to the radiological imaging unit 3. The tracking unit may be separate from the imaging unit, or it may be integrated into it. The electromagnetic field generator is integral part of the electromagnetic tracking unit 6. Multiple electromagnetic sensors may be integrated into the instrument 5, allowing simultaneous localization of multiple points, and supporting reconstruction of the shape of a segment of the instrument 5 comprising and connecting the localized points.

In an alternative embodiment, the tracking of the temporal location of the instrument is derived from laser radiation. For optical tracking, the instrument comprises multiple optical fibers or a multi-core optical fiber extending from distal end 52 to a proximal portion of the instrument, typically the handgrip 51, where optical connection to the optical tracking unit 6 is facilitated. The optical tracking unit 6 comprises a laser radiation generator configured to transmit laser radiation into at least an optical fiber in the instrument, and an optical detector configured to receive reflections from within the at least an optical fiber. The shape of the at least an optical fiber, hence that of the instrument 5 is derived by processing optical reflection signals from within the optical fibers, received by a detector. The reflections of laser radiation from within the at least an optical fiber are indicative of local strains to which the instrument 5 is exposed in tortuous vessel branch. Shape determination of a medical instrument is described in WO2008131303 A2 with more details. Optical shape sensing makes possible the localization of any points along the at least an optical fiber integrated into the instrument 5 at all instances.

A further alternative location tracking technique of the instrument is based on ultrasound. An ultrasound sensor is integrated into the distal tip 52 of the instrument 5. The ultrasound tracking unit 6 comprises electronics for driving an ultrasound probe which is either directly coupled onto the body of the person 2 or it is mounted onto the support means 4 such that the field of view of the ultrasound probe covers the region of interest of the target vasculature. Upon excitation of the external ultrasound probe with an electric signal, the generated ultrasound signal is transmitted into the body of the person 2 and a portion of the ultrasound signal is received by the ultrasound sensor integrated into the distal tip 52 of the instrument 5. The time of flight of the ultrasound signal is indicative of the position of the distal tip 52 of the instrument with respect to the external ultrasound probe.

A further alternative location tracking technique of the instrument is based on electrical impedance measurement. Electrical signals are sent into the patient by multiple electrically conductive patches distributed onto the body of the person 2. The distal end 52 of the trackable instrument 5 comprising an electrically conductive electrode receives the electrical signals which are transmitted to the tracking unit 6. The electrical impedances derived from the received electrical signals are indicative of the location of the conductive electrode on the distal tip 52 in the region of interest comprising the target vasculature.

Figure 2:
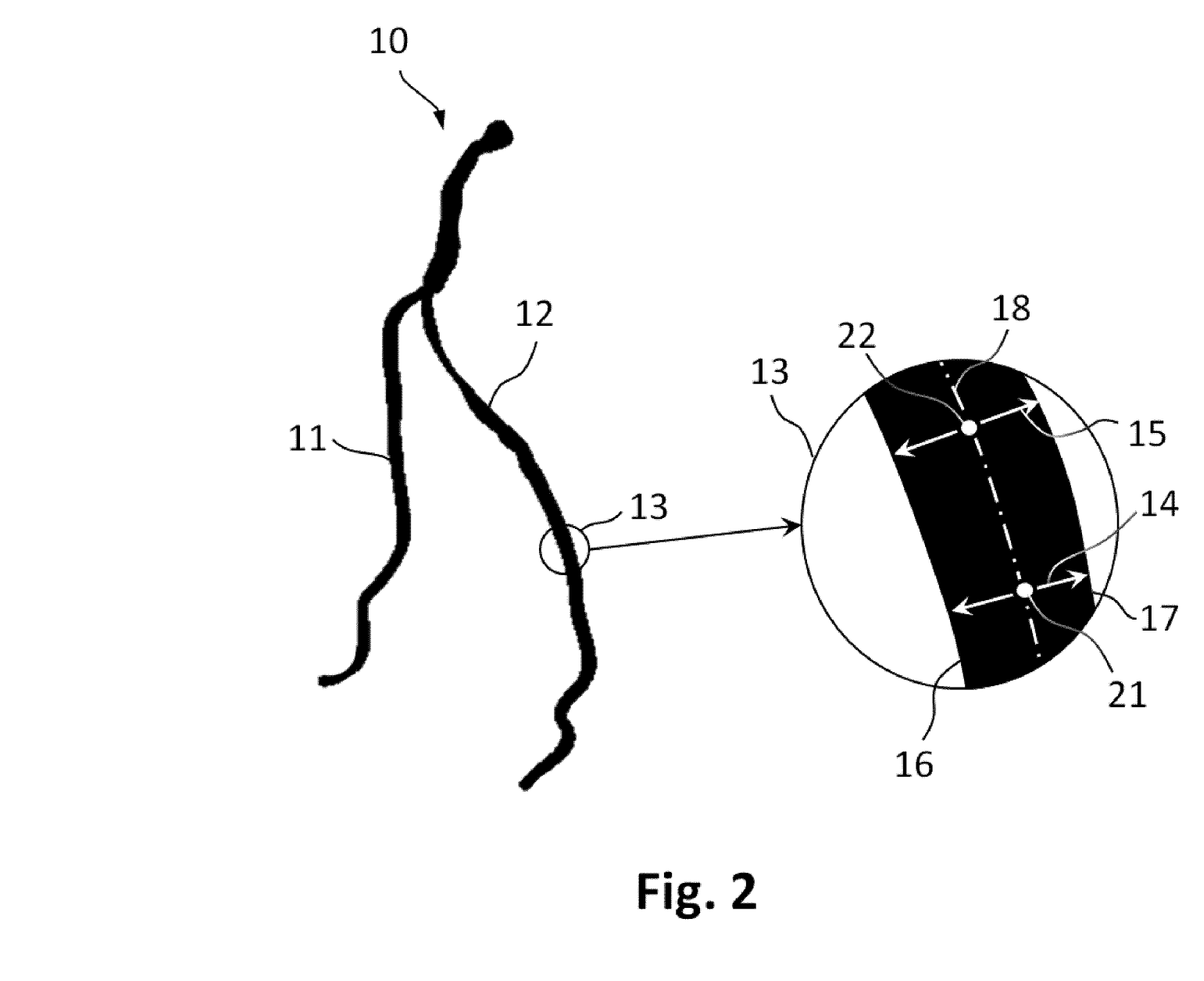
FIG. 2 shows an exemplary angiographic projection of a branching vessel and the method of local vessel diameter calculation.

The system further comprises an apparatus 7 for characterizing a vessel of a person 2. The apparatus 7 is configured to be coupled to the radiological imaging unit 3 for generating morphological projection information of the vessel. An exemplary two-dimensional angiographic projection 10 is illustrated in FIG. 2, where the vasculature comprises two branches 11 and 12. In the magnified portion 13 of the right vessel branch 12 a first diameter 14 and a second diameter 15 of the vessel are ascertained at two distinct locations 21,22 by measurement of the distance between the two outer borders 16,17 in a perpendicular direction to the center line of the two-dimensional angiographic vessel projection. The two diameters 14,15 correspond to the first and second temporal locations 21,22 of the tracked instrument 5, which are subsequent temporal positions of a point of a moving instrument, like schematically and exemplarily illustrated in FIG. 3. Alternatively, the two distinct positions of the instrument can be two different points of a position tracked instrument that is immobile with respect to the person 2 at the entry site into the vasculature, as illustrated in FIG. 4.

Figure 3:
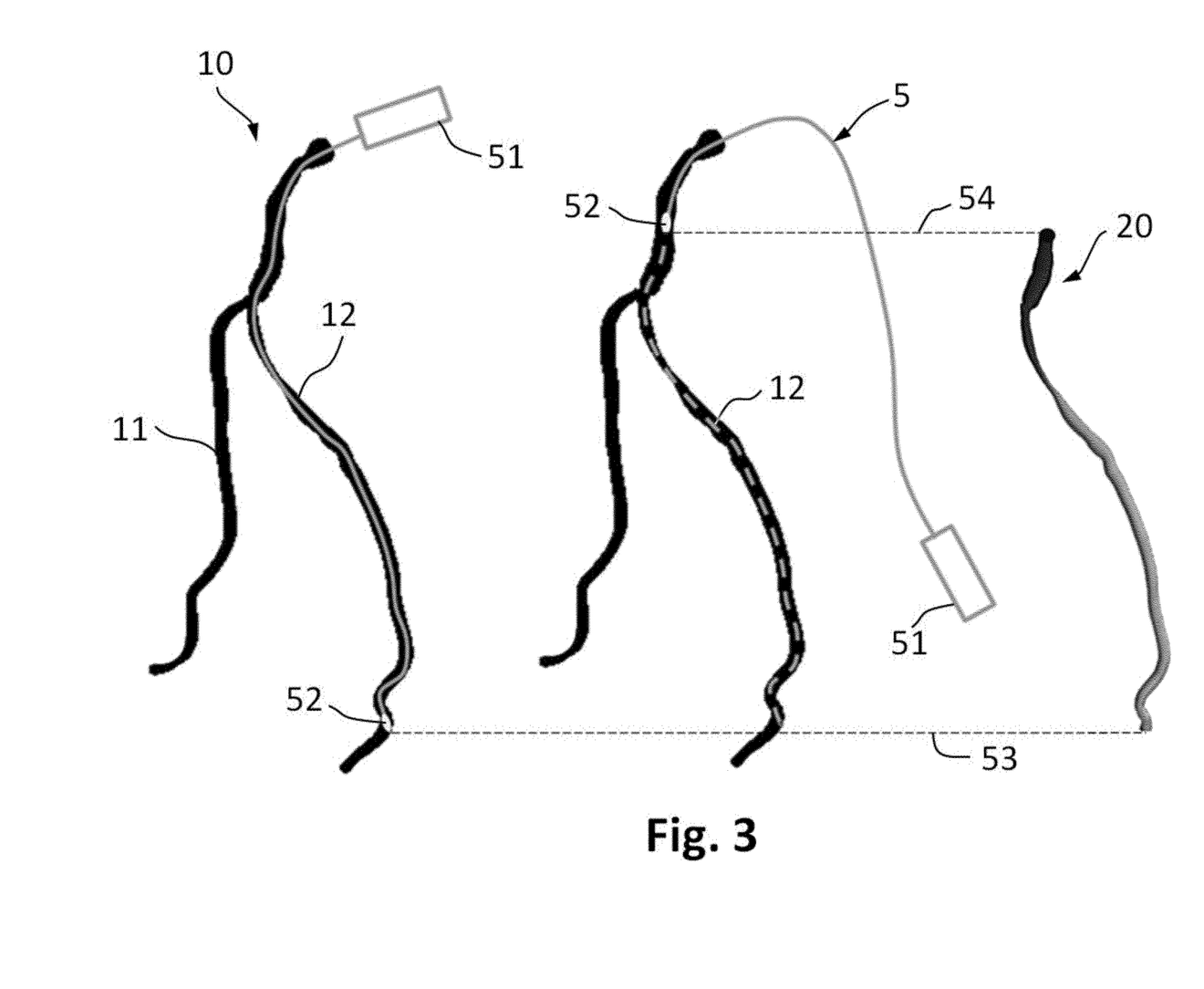
FIG. 3 shows an exemplary embodiment of a three-dimensional morphological vessel model rendered according to the invention based on an angiographic projection and electromagnetic tracking of an instrument.

FIG. 3 shows an exemplary embodiment of a three-dimensional morphological vessel model 20 rendered according to the invention based on an angiographic projection 10 and electromagnetic tracking of an instrument 5. The location of the instrument 5 in the vasculature of the person 2 is tracked by sensing the strength of an electromagnetic field with an electromagnetic sensor in the distal tip 52 of the instrument 5. The distal tip 52 is withdrawn in the vessel branch 12 from a position 53 to a position 54. During the withdrawal the location of the distal tip 52 is continuously tracked and the diameters of the vessel branch are determined for all those locations. The registration of the two-dimensional angiographic projection to the location information of the distal tip is simple, since the metallic electromagnetic coil is considerably visible on a real-time x-ray projection after the contrast bolus has been diluted and carried away by the blood stream. An alternative solution is to use radiological marker on the distal tip of the instrument, placed in the transversal cross section through the center point of the integrated electromagnetic sensor coil. Once the temporal location information of the instrument is registered with the temporal location of the instrument in the two-dimensional morphological information of the vessel, the three-dimensional morphological vessel model 20 is generated along withdrawal path of the distal tip 52, extending between positions 53 and 54. Similar approach for construction of the three-dimensional vessel model 20 can be implemented when tracking the distal tip 52 of the instrument 5 based on ultrasound or electrical impedance.

Figure 4:
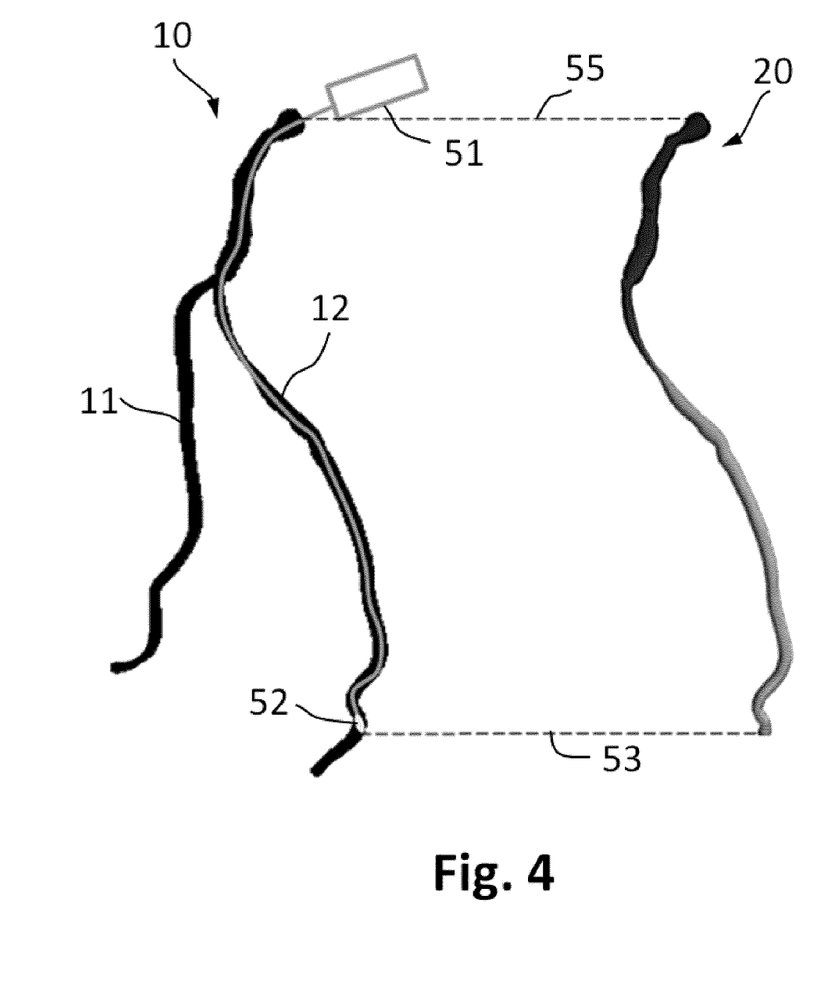
FIG. 4 shows an exemplary embodiment of a three-dimensional morphological vessel model rendered based on an angiographic projection and optical shape tracking of an instrument.

FIG. 4 shows an exemplary embodiment of a three-dimensional morphological vessel model 20 rendered based on an angiographic projection 10 and optical shape tracking of an instrument 5. The shape of the at least an optical fiber integrated in the instrument 5, hence that of the instrument 5, is derived by processing optical reflection signals from within the optical fibers indicative of local strains to which the instrument 5 is exposed in the tortuous vasculature. The position of any points along the optical fiber in the target vasculature up to the position 55 is determined by the optical shape sensing technique at all instances, hence the instrument may be maintained in stationary position with respect to the entry site into the vasculature of the person 2. The registration of the two-dimensional angiographic projection 10 to the location information of the instrument 5 along the vessel branch 12 can be achieved by using radiological markers on the instrument 5. Similar to the optical shape sensing technique, three-dimensional morphological vessel model can be constructed without withdrawing the instrument with respect to the vessel branch 12 by using electromagnetic, ultrasound or electrical impedance based tracking, in case that the instrument 5 comprises multiple electromagnetic sensors, ultrasound sensors or electrodes integrated into the instrument 5 along its elongated body.

In an embodiment, the apparatus may further be configured to detect phase signal from the measurement information received from the tracking unit 6 or from the imaging unit 3, being indicative of motion phases of a periodic movement originating from cardiac and/or respiratory motion. The phase signal of cardiac motion can be derived from electrical information acquired by at least one of an electrode integrated into the instrument 5, or an electrode patch attached to the body of the person 2, which may be having also electrical impedance instrument tracking functionality. Alternatively, the phase signal can be derived from ultrasound measurement information used also for ultrasound based instrument tracking. The cyclical motion creates cyclical interaction of the tracked instrument with the vessel structure, which results in cyclical pattern in the acquired ultrasound information. Similarly, the phase signal can be derived from real-time radiological information acquired by the radiological imaging unit, on the premises that the tracked instrument is detectable by the radiological imaging unit, which is the case when electromagnetic sensor coil or radiological markers are integrated into the instrument. The processor can assign the first and second diameters of the vessel in a three-dimensional morphological model based on gating to the phase of the cyclical cardiac motion. In such way a three-dimensional morphological model is generated for each phase. The three-dimensional morphological models may be displayed on a screen in a consecutive order, corresponding to the respective timing in the cyclical motion.

In an alternative embodiment, the apparatus may further be configured to derive a first and a second diameter for each consecutive phase of the cyclical cardiac motion from the morphological projection 10 information corresponding to a first and a second temporal location 21,22 of the instrument, then to assign the first and second diameters 14,15 of the vessel in a three-dimensional morphological model 20 of the vessel at locations defined by the first and second temporal locations 21,22 of the instrument for each consecutive phase of the cyclical cardiac motion.

Figure 5:
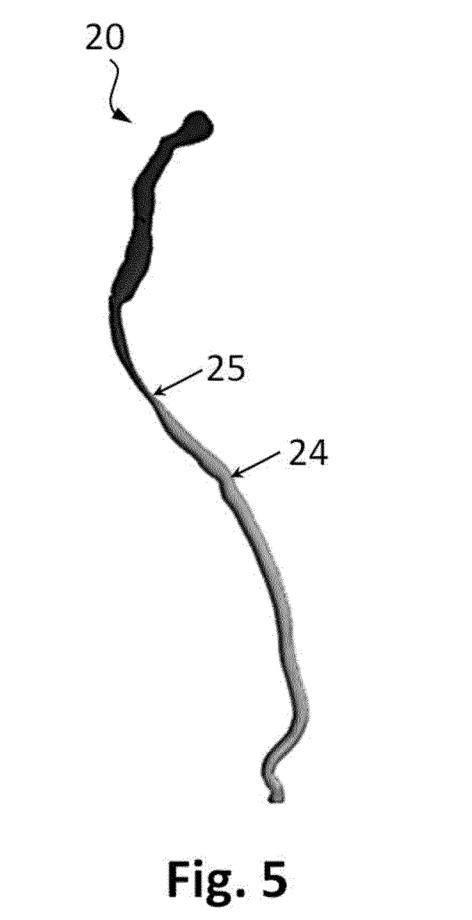
FIG. 5 shows a schematic and exemplary embodiment of a three-dimensional morphological vessel model with assigned physiological information.

FIG. 5 shows a schematic and exemplary embodiment of a three-dimensional morphological vessel model 20 with assigned physiological information. A sensor may be integrated into the distal end 52 of the instrument 5, and additional sensors may be integrated into the elongated body of the instrument 5. Typical sensors may be pressure sensors or flow sensors. The measurement information is transmitted to the apparatus 7, where the processor is configured to assign at least a first physiological information 24 to the three-dimensional morphological model 20 of the vessel at the location defined by the first temporal location of the instrument. In an alternative embodiment of the system, the processor is further configured to assign at least a second physiological information 25 to the three-dimensional morphological model 20 of the vessel at a location defined by the second temporal location of the instrument. The assigned physiological information may be quantities as measured, such as blood pressure or blood flow velocity, or they may be physiological information derived from the measurements, which may represent either FFR or blood flow resistance according to:

$$FFR = P_d/P_a \quad \text{(Eq. 1)}$$

$$P_a - P_d = R \cdot Q + V \cdot Q^2 \quad \text{(Eq. 2)}$$

where $P_d$ is the blood pressure distal to the first temporal location of the instrument, $P_a$ is the blood pressure proximal to the first temporal location of the instrument, R is the linear blood flow resistance, V is the quadratic blood flow resistance and Q is the volumetric blood flow rate. The parameters of Eq. 2 can be determined by using a lumped component method. The physiological information 24 and 25 may be represented as discrete values on the three-dimensional morphological vessel model 20, or alternatively the vessel model may be color-coded according to a colormap indicative of values of the physiological information. At a specific temporal location of the instrument multiple physiological information may be assigned to the three-dimensional morphological vessel model 20.

Figure 6:
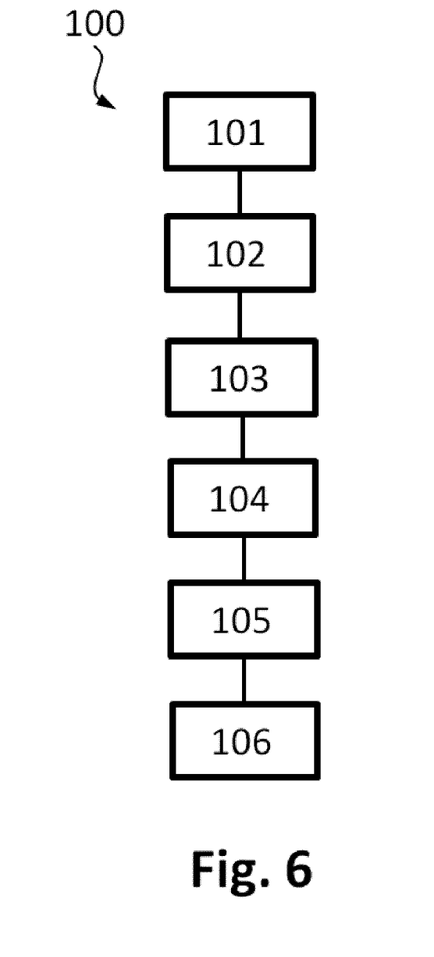
FIG. 6 schematically and exemplarily illustrates the steps of a method for characterizing a vessel of a living being.

A method 100 for characterizing a vessel of a living being is presented schematically in FIG. 6, the method comprising the following steps: 101 introducing a trackable instrument 5 into the vessel, 102 measuring temporal location information of the instrument 5 in the vessel, 103 generating morphological projection 10 information of the vessel, 104 deriving a first and a second diameter of the vessel from the morphological projection 10 information corresponding to a first and a second temporal location of the instrument, and 105 assigning the first and second diameters of the vessel in a three-dimensional morphological model of the vessel at locations defined by the first and second temporal locations of the instrument. The method may additionally comprise the step 106 of rendering a graphical representation of the three-dimensional morphological model 20 with the assigned first and second diameters on a display 71.

In an alternative embodiment of the method 100, the step 104 of deriving the first and second diameters 14,15 and the step 102 of measuring the first and second temporal locations 21,22 of the instrument are performed for consecutive phases of a cyclical motion, and the step 105 of assigning the first and second diameters 14,15 of the vessel in the three-dimensional morphological model 20 of the vessel at locations defined by the first and second temporal locations 21,22 of the instrument is performed for respective consecutive phases of the cyclical motion. Each three-dimensional morphological model 20 based on gating according to different phases of the cyclical cardiac motion and/or respiratory motion may represent a frame, and the frames may be rendered on a display in step 106 in consecutive order corresponding to the respective timing in the cyclical motion, resulting in a movie appearance on the display 71. Such visual representation allows immediate assessment of reactions to various agents, for instance vasodilators for producing hyperemia administered simultaneously with contrast agent bolus.

Although medical device was used in the exemplary description of the invention, that should not be construed as limiting the scope.

Other variations to the disclosed embodiments can be understood and effected by those skilled in the art in practicing the claimed invention, from a study of the drawings, the disclosure, and the appended claims.

A single unit or device may fulfill the functions of several items recited in the claims. The mere fact that certain measures are recited in mutually different dependent claims does not indicate that a combination of these measures cannot be used to advantage.

In the claims, the word "comprising" does not exclude other elements or steps, and the indefinite article "a" or "an" does not exclude a plurality.

Any reference signs in the claims should not be construed as limiting the scope.

The invention claimed is:

1. An apparatus for characterizing a vessel of a living being, the apparatus comprising:
    a processor,
    wherein the apparatus is configured to be coupled to:
        a tracking unit for continuously measuring location information of a trackable instrument in a vessel lumen of the vessel over time as the trackable instrument moves from a first location within the vessel lumen at a first time to a second location within the vessel lumen at a second time; and
        an imaging unit for generating a projection image of the vessel; wherein the processor is configured to:
    responsive to the trackable instrument being positioned at the first location at the first time:
        identify, within the projection image, first outer borders of the vessel lumen at the first location; and
        determine, based on the projection image, a first distance between the first outer borders;
    responsive to the trackable instrument being positioned at the second location at the second time:
        identify, within the projection image, second outer borders of the vessel lumen at the second location; and
        determine, based on the projection image, a second distance between the second outer borders;
    successively generate a different portion of a three-dimensional morphological model of the vessel as the trackable instrument moves through a respective segment of the vessel lumen positioned between the first location and the second location such that the different portions of the three-dimensional morphological model correspond to the respective segments of the vessel lumen extending from the first location to the second location, wherein a first diameter of a first portion of the three-dimensional morphological model corresponding to the first location comprises the first distance and a second diameter of a second portion of the three-dimensional morphological model corresponding to the second location comprises the second distance; and
    output, to a display in communication with the processor, a graphical representation of the three-dimensional morphological model of the vessel.

2. The apparatus according to claim 1, wherein the projection image of the vessel is derived from angiography.

3. The apparatus according to claim 1, wherein the first location of the trackable instrument at the first time and the second location of the trackable instrument at the second time are derived from electromagnetic signals.

4. The apparatus according to claim 1, wherein the first location of the trackable instrument at the first time and the second location of the trackable instrument at the second time originate at same phase of a cyclical cardiac or breathing motion of the living being.

5. The apparatus according to claim 1, further comprising:
    the trackable instrument for introduction into the vessel of the living being;
    the tracking unit for continuously measuring the location information of the trackable instrument in the vessel; and
    the imaging unit for generating the projection image of the vessel.

6. The apparatus according to claim 5, wherein the trackable instrument comprises a sensor for measuring physiological information, and wherein the processor is further configured to:
    assign, based on the location information, at least a first physiological information measured by the sensor at the first location to the first portion of the three-dimensional morphological model of the vessel; and
    output, to the display, a graphical representation the first physiological information, wherein the graphical representation of the first physiological information is positioned adjacent to the first portion in the graphical representation of the three-dimensional morphological model.

7. The apparatus according to claim 6, wherein the processor is further configured to:
    assign, based on the location information, at least a second physiological information measured by the sensor at the second location to the second portion of the three-dimensional morphological model of the vessel; and
    output, to the display, a graphical representation of the second physiological information, wherein the graphical representation of the second physiological information is positioned adjacent to the second portion in the graphical representation of the three-dimensional morphological model.

8. The apparatus according to claim 7, wherein the physiological information is at least one of a blood pressure, a blood flow velocity, fractional flow reserve (FFR), or a blood flow resistance.

9. The apparatus according to claim 7, wherein the trackable instrument comprises at least an electromagnetic sensor, the tracking unit comprises an electromagnetic field generator, and the imaging unit is a radiological imaging unit.

10. The apparatus according to claim 1, wherein:
    to identify the first outer borders of the vessel lumen and determine the first distance between the first outer borders, the processor is configured to identify the first outer borders and determine the first distance between the first outer borders for each consecutive phase of a cyclical motion indicative of a cardiac or a breathing motion of the living being;

to identify the second outer borders of the vessel lumen and determine the second distance between the second outer borders, the processor is configured to identify the second outer borders and determine the second distance between the second outer borders for each consecutive phase of the cyclical motion; and to successively generate the different portion of the three-dimensional morphological model of the vessel, the processor is configured to successively generate the different portion of the three-dimensional morphological model of the vessel for each consecutive phase of the cyclical motion.

11. A method for characterizing a vessel of a living being, comprising:

continuously measuring location information of a trackable instrument in a vessel lumen of the vessel over time as the trackable instrument moves from a first location within the vessel lumen at a first time to a second location within the vessel lumen at a second time;

generating a projection image of the vessel;

responsive to the trackable instrument being positioned at the first location at the first time:
identifying, within the projection image, first outer borders of the vessel lumen at the first location; and
determining, based on the projection image, a first distance between the first outer borders;

responsive to the trackable instrument being positioned at the second location at the second time:
identifying, within the projection image, second outer borders of the vessel lumen at the second location; and
determining, based on the projection image, a second distance between the second outer borders;

successively generating a different portion of a three-dimensional morphological model of the vessel as the trackable instrument moves through a respective segment of the vessel lumen positioned between the first location and the second location such that the different portions of the three-dimensional morphological model correspond to the respective segments of the vessel lumen extending from the first location to the second location, wherein a first diameter of a first portion of the three-dimensional morphological model corresponding to the first location comprises the first distance and a second diameter of a second portion of the three-dimensional morphological model corresponding to the second location comprises the second distance; and outputting, to a display, a graphical representation of the three-dimensional morphological model of the vessel.

* * * * *